(12) United States Patent
Jackson, III

(10) Patent No.: US 6,855,105 B2
(45) Date of Patent: Feb. 15, 2005

(54) ENDOSCOPIC PEDICLE PROBE

(76) Inventor: Avery M. Jackson, III, Michigan Neurosurgical Institute 4620 Genesys Pkwy., Grand Blanc, MI (US) 48439-8067

(*) Notice: Subject to any disclaimer, the term of this patent is extended or adjusted under 35 U.S.C. 154(b) by 159 days.

(21) Appl. No.: 10/193,501

(22) Filed: Jul. 11, 2002

(65) Prior Publication Data

US 2003/0013936 A1 Jan. 16, 2003

Related U.S. Application Data

(60) Provisional application No. 60/304,279, filed on Jul. 11, 2001.

(51) Int. Cl.[7] .................................................. A61B 1/00
(52) U.S. Cl. ...................... 600/109; 600/114; 600/160; 600/129
(58) Field of Search ................................ 600/104, 114, 600/121, 109, 106, 160, 129; 606/185, 167, 205; 604/164–167, 264, 272

(56) References Cited

U.S. PATENT DOCUMENTS 5,573,537 A    11/1996   Rogozinski ................... 606/80
5,609,562 A  * 3/1997    Kaali .......................... 600/114
5,685,820 A  * 11/1997   Riek et al. ................... 600/114
6,387,043 B1 * 5/2002    Yoon ........................... 600/109
6,425,859 B1 * 7/2002    Foley et al. ................. 600/204

OTHER PUBLICATIONS

Photograph of ACI tapered Reamer model TR–3 by Alberta Custom Instruments Ltd. of Edmonton, Alberta Canada. In use since approximately 1987.

* cited by examiner

Primary Examiner—Beverly M. Flanagan
(74) Attorney, Agent, or Firm—Dennis H. Lambert

(57) ABSTRACT

An endoscopic pedicle probe for use during spinal surgery to form a hole in a pedicle for reception of a pedicle screw. The probe has an enlarged proximal end for cooperation with the hand of the surgeon so that the probe can be pushed through the pedicle in a controlled manner, and an elongate hollow shaft terminating in a distal tip end. A fiber optic cable or endoscope is placed in the hollow shaft and connected with a monitor to enable the surgeon to visually observe the structure adjacent the tip end of the probe during surgery, whereby the probe may be accurately placed in the pedicle for subsequent accurate placement of the pedicle screw in the hole formed with the probe.

8 Claims, 4 Drawing Sheets

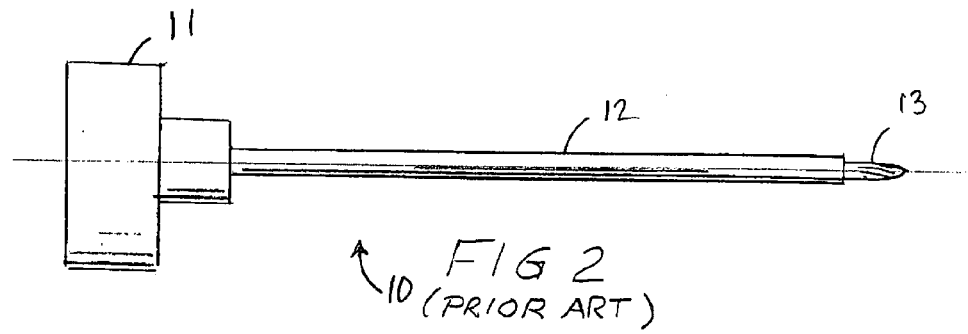
FIG 2 (PRIOR ART)
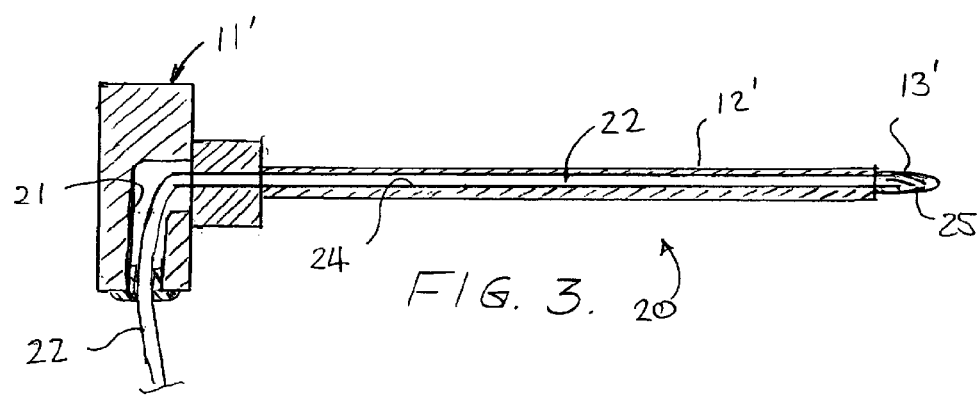
FIG. 3.
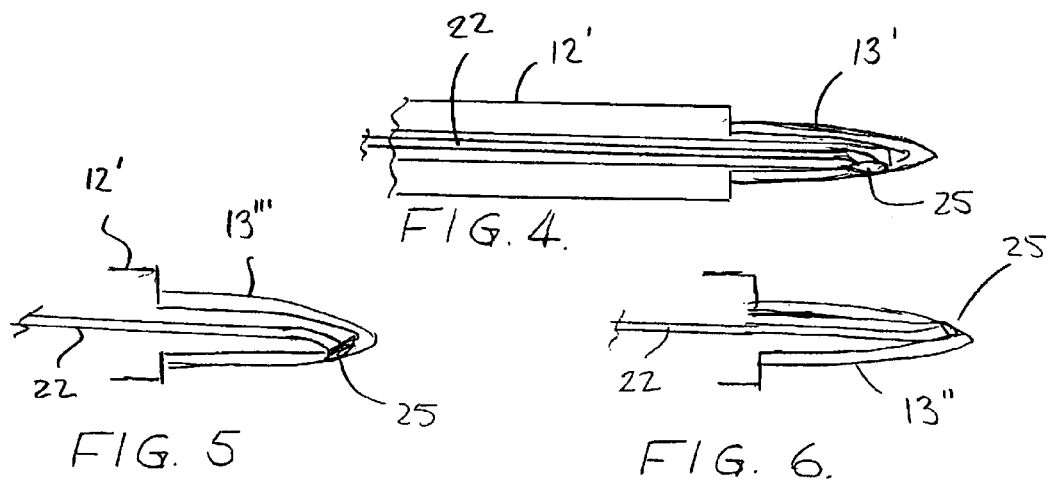
FIG. 4.
FIG. 5
FIG. 6.

ENDOSCOPIC PEDICLE PROBE

This application claims the benefit of U.S. provisional application Ser. No. 60/304,279, filed Jul. 11, 2001, entitled ENDOSCOPIC PEDICLE PROBE.

BACKGROUND OF THE INVENTION

1. Field of the Invention

This invention relates generally to surgical instruments. More specifically, the invention relates to a pedicle probe for use in forming holes in a vertebral pedicle in preparation for pedicle screw insertion.

2. Prior Art

It is sometimes necessary to perform surgery on the spine in order to repair trauma, correct a deformity, or alleviate the effects of disease. Spinal fusion or stabilization is one procedure that may be employed to treat these conditions.

Spinal fusion may be accomplished by insertion of screws into the pedicle to stabilize a spinal segment. The pedicle is a dense, stem-like structure projecting from the posterior of a vertebra, and there are two pedicles per vertebra that connect to other structures. Since the pedicle is the strongest point of attachment of the spine, significant forces can be applied to the spine without failure of the bone-to-metal connection.

To insert pedicle screws, a long, thin, metal probe is inserted through the pedicle and into the vertebral body, forming a hole for reception of the screw. A variety of probes are known in the prior art, including the so-called gear shift pedicle probe and the Fox pedicle probe. The gear shift probe has a round head on its proximal end, whereas the Fox probe has a flat disc-shaped head on its proximal end.

Conventional modalities used to approximate or simulate screw placement are indirect, and include fluoroscopic guidance and frameless stereotactic guidance. Approximations of the pedicle and surrounding vital structures are obtained from a CT scan or MRI done prior to surgery.

Conventional pedicle probes may be straight or curved, and comprise an elongate solid metal shaft with an enlarged hand grip on the proximal end. The probe may have a shaped distal end adapted for forming a hole through the pedicle, or a separate awl or reamer may first be used to form a hole through the pedicle, and the probe then inserted into the cancellous bone of the pedicle and into the vertebral body to develop a path for the screw.

Proper positioning of a conventional probe depends to an extent upon tactile feel. For instance, advancement of the probe should be smooth and consistent. A sudden plunge suggests breaking out of the pedicle laterally, and an increase in resistance indicates abutment against the pedicle or vertebral body cortex.

These conventional modalities require a steep learning curve, and improper or inaccurate manipulation of the probe and placement of the pedicle screw can result in caudal or medial penetration of the pedicle cortex and dural or neural injury.

Currently, there is no direct way to confirm that the hole was made within the pedicle and that the screw will be placed completely inside the pedicle. Surrounding structures can be injured if a portion of the screw is placed outside of the pedicle. There can be nerve root injury, epidural vessel injury, or spinal fluid leakage caused by a misplaced screw.

Accordingly, there is need for a system and method for insertion of pedicle screws which eliminates the guesswork and error-prone modalities of the prior art. In particular, there is need for a system which provides the surgeon with direct confirmation during the surgical procedure that the pedicle probe is in the right position for forming a hole for proper placement of the pedicle screw.

SUMMARY OF THE INVENTION

The present invention comprises a pedicle probe having means associated with it to enable the surgeon to directly confirm the location of the probe during a surgical procedure. More specifically, the invention comprises a pedicle probe which provides the surgeon with a visual indication during a surgical procedure of the position of the probe relative to the pedicle and surrounding structure.

In particular, the probe of the invention is an endoscopic probe having an elongate hollow shaft with a fiber optic bundle or endoscope extending through it. The endoscope or fiber optic bundle is connected with a conventional endoscopic monitor, and a lens in the distal end of the probe affords the surgeon views ranging from 0° to 90°.

In a specific example of the invention, a Fox probe is modified to have a hollow shaft and a small endoscope or fiber optic bundle is placed in the hollow shaft. A lens is positioned in the distal end of the shaft and connected with the fiber optic bundle or endoscope to afford either a 0°, a 45° or a 90° view. The endoscope is connected with a conventional endoscope monitor.

The endoscopic pedicle probe of the invention puts the surgeon "in the pedicle" with the use of endoscopy. The positioning of the probe can be directly and accurately determined during surgery, and there is no question as to whether the screw will be too medial, lateral, cranial, caudal, or deep. The surgeon will know if the wall of the pedicle has been breached, and to what extent. He or she can then decide to use the planned trajectory even if there is a small breach of the pedicle wall. The probe of the invention provides the surgeon with knowledge of how much of an intrusion exists, and he or she can ascertain if critical structures will be in danger from screw placement. The surgeon can also avoid parallax that may cause errors when using fluoroscopic guidance.

Further, a probe must be used in any event to perform spinal fusions, and the probe of the invention will not represent an additional instrument needed for pedicle screw placement. Accordingly, there will be no additional costs or equipment needed to perform the standard spinal fusion.

The probe of the invention can be utilized in the cervical spine for lateral mass screw placement, pedicle screw placement, or trans articular screw placement. It can be used in the thoracic, lumbar, and sacral spine for pedicle screw placement and translaminar screw placement, and can be used in standard open spine fusion or in minimally invasive percutaneous spine fusion.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein:

FIG. 2 is a side view in elevation of a conventional pedicle probe on which the present invention can be based;

FIG. 3 is a longitudinal sectional view of the endoscopic pedicle probe of the invention, showing the hollow interior and fiber optic cable or endoscope therein;

FIG. 4 is an enlarged, fragmentary, longitudinal sectional view of the distal end of the endoscopic pedicle probe of the invention, depicting a 90° lens therein;

FIG. 5 is a view similar to FIG. 4, showing a 45° lens therein;

FIG. 6 is a view similar to FIG. 5, showing a 0° lens therein;

DETAILED DESCRIPTION OF THE PREFERRED EMBODIMENTS

Figure 1:
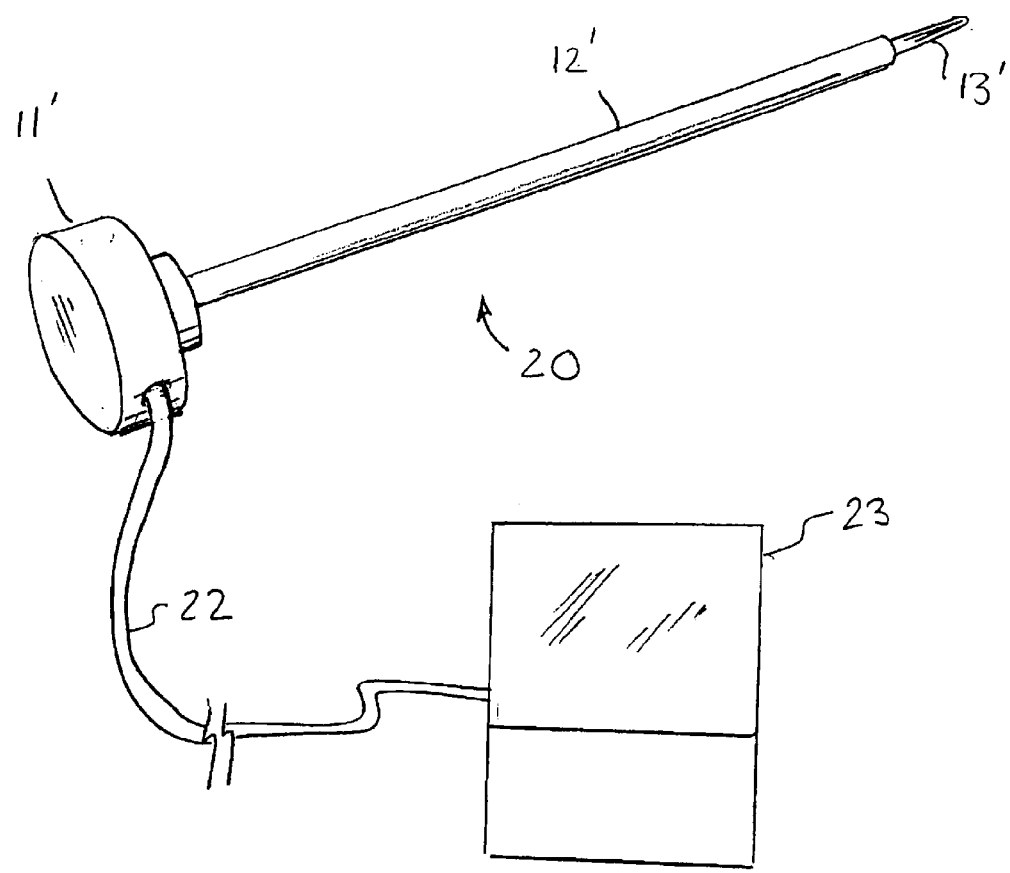
FIG. 1 is a somewhat schematic perspective view of an endoscopic pedicle probe according to the invention, in combination with conventional endoscopy monitor.
Figure 9:
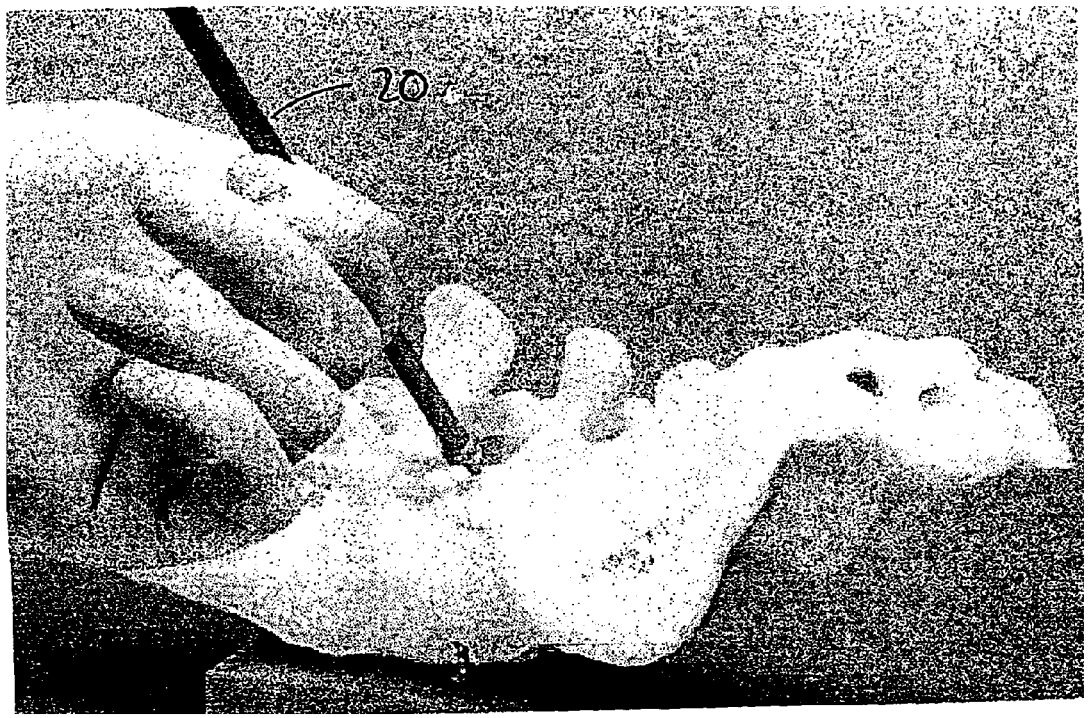
FIG. 9 is a perspective view depicting how a pedicle probe is used to form a hole in a pedicle.

Referring more specifically to the drawings, a conventional Fox pedicle probe is depicted at 10 in FIG. 2. The probe has a disc-shaped proximal end 11 that is about two inches in diameter, and a solid metal shaft 12 projecting from the center of one side thereof. A tip end 13 configured to act as a reamer, i.e., with a fluted configuration as found on drill bits, is on the distal end of the shaft. In use, a surgeon places the disc-shaped proximal end 11 in the palm of his or her hand, with the shaft extending forwardly. The tip end is then pushed against the pedicle while being rotated back and forth about the longitudinal axis of the shaft to form a hole in the pedicle for reception of a pedicle screw. See, for example, FIGS. 9–13.

In the specific embodiment illustrated and described herein, the pedicle probe 20 of the invention, as shown in FIGS. 1 and 3–13, is based on the Fox pedicle probe of FIG. 2. However, it should be understood that the probe 20 could be based on other commercially available probes, or could embody a completely new design. The disc-shaped proximal end 11' of the probe 20 has an opening 21 formed in it for receipt of a fiber optic cable or endoscope 22, which is connected with a suitable conventional monitor 23. Similarly, the shaft 12' has a bore 24 formed through its length for receipt of the fiber optic cable or endoscope 22, which terminates in the tip end 13' at a lens 25. As in conventional pedicle probes, such as the Fox pedicle probe, the tip end 13' is adapted to penetrate the hard bony tissue of a vertebral pedicle to form a hole for reception of a pedicle screw. As shown in the drawings, the tip end has a reduced, substantially uniform diameter throughout its length, and has a sharpened point. The diameter of the tip end is approximately the same as, or slightly smaller than, the diameter of a pedicle screw to be inserted in the hole formed with the probe, and will form an elongate hole having a uniform diameter for secure engagement with a screw inserted in the hole. The tip has a hardness and configuration to act as a reamer, preferably with a fluted configuration as found on drill bits and as incorporated in a conventional Fox pedicle probe, to facilitate penetration of the probe through the hard bony tissue.

As shown in FIGS. 4, 5 and 6, respectively, the tip end 13' or 13" or 13'" can be configured to position the lens 25 for providing a 90° view, or a 45° forward view, or a 0° view (straight ahead). Thus, by selection of an appropriate probe, or by appropriate manipulation of a probe, the surgeon can obtain a direct visual indication of the exact position of the probe in the pedicle and of the pedicle itself and surrounding structure. As depicted in these Figures, the lens is placed rearwardly of the distal point of the end to protect it when the probe is pressed against and pushed through hard bony tissue.

Figure 7:
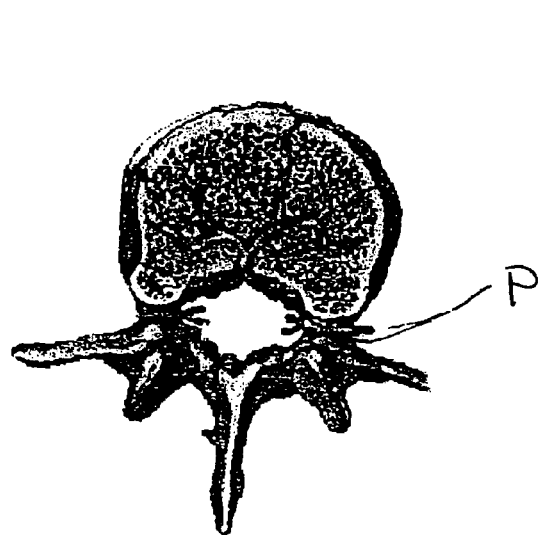
FIG. 7 is an axial view of a pedicle.
Figure 8:
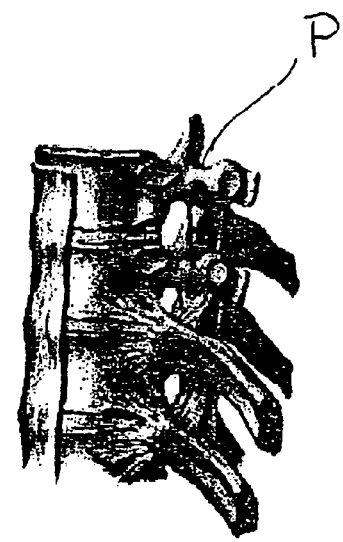
FIG. 8 is a sagittal view of a pedicle.
Figure 10:
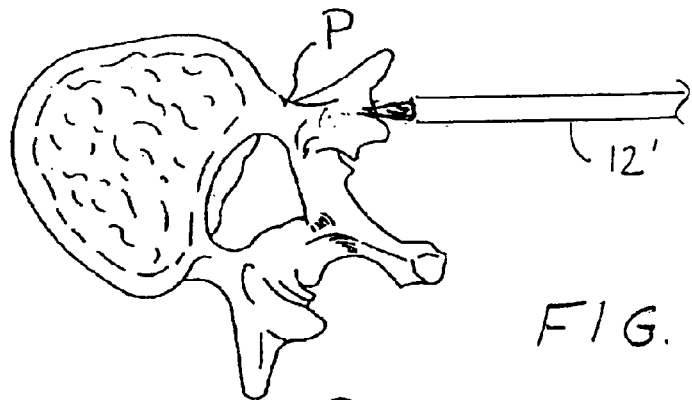
FIGS. 10–13 are somewhat schematic views depicting the progressive steps in forming a hole in the pedicle using the pedicle probe.
Figure 11:
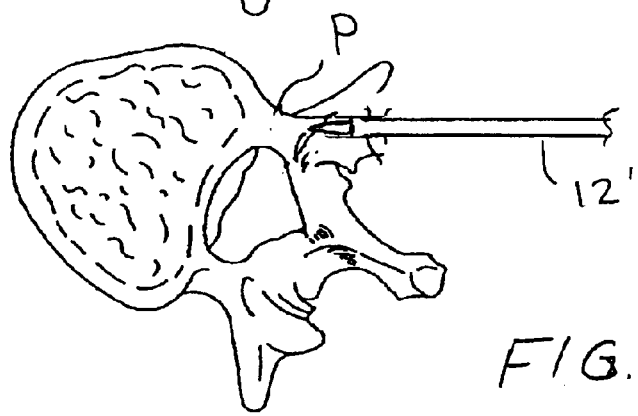
Figure 12:
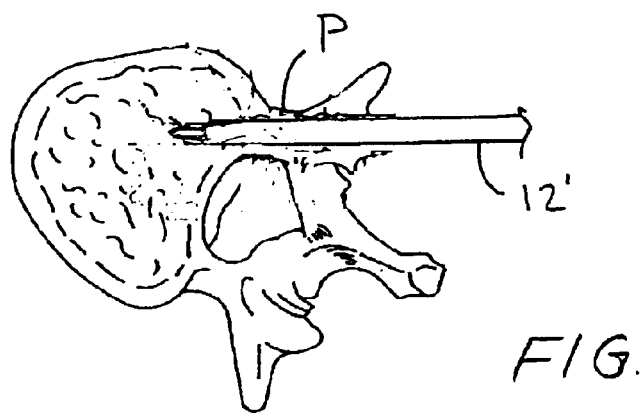
Figure 13:
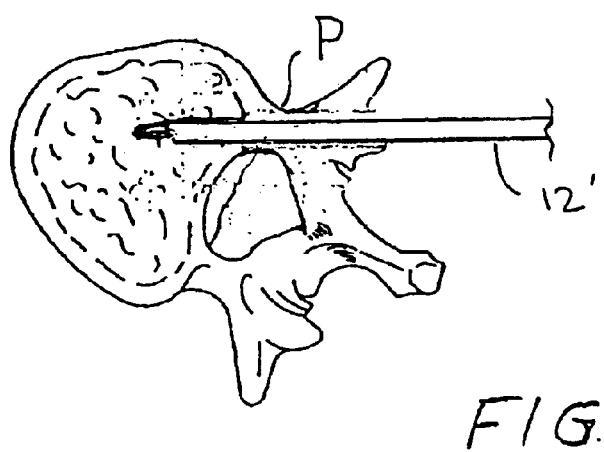

FIGS. 7 and 8 are axial and sagittal views, respectively, of a pedicle P, and FIGS. 9–13 are schematic illustrations of how a probe 20 might be used to form a hole in the pedicle. Thus, and as seen especially in FIGS. 10–13, the probe is pushed through the pedicle to form a hole for reception of a pedicle screw (not shown). Depending upon the structure of the tip end 13' the probe also may be rotated back and forth to assist in forming the hole. Great care must be exercised to insure that the probe stays within the pedicle and does not break through the wall, or does not go too deep, etc.

The endoscopic probe of the invention provides the surgeon with a direct visual indication of the exact location of the probe, whereby the hole can be formed with accuracy and precision.

While particular embodiments of the invention have been illustrated and described in detail herein, it should be understood that various changes and modifications may be made to the invention without departing from the spirit and intent of the invention as defined by the scope of the appended claims.

What is claimed is:

1. An endoscopic pedicle probe for forming a hole in the hard bony tissue of a vertebral pedicle to receive a pedicle screw, comprising:

an enlarged proximal end for cooperation with the hand of the surgeon to aid in controlling the probe;

an elongate hollow shaft having a longitudinal axis and extending from the enlarged proximal end and terminating in a distal end;

a shaped tip end on the distal end of the shaft, having a reduced, substantially uniform diameter and a hardness and configuration adapted to be pushed through a pedicle to form a hole for reception of a pedicle screw; and means in the hollow shaft and connected with an external monitor for conveying a visual image of the position of the distal end of the probe during a surgical procedure, whereby a surgeon is provided with direct visual indication of the exact position of the probe during spinal surgery.

2. An endoscopic pedicle probe as claimed in claim 1, wherein:

the proximal end of the probe is disc-shaped and is modified to receive an endoscope.

3. An endoscopic pedicle probe as claimed in claim 2, wherein:

a lens is positioned in the tip end of the shaft and is connected through the endoscope with a monitor to enable objects adjacent the distal end of the shaft to be viewed by a surgeon using the probe.

4. An endoscopic pedicle probe as claimed in claim 3, wherein:

the tip end is fluted like a drill bit, and the lens and opening for receipt of the lens is positioned in the base of a channel formed between the flutes.

5. An endoscopic pedicle probe as claimed in claim 3, wherein:

the lens is positioned rearwardly of the distal point of the tip end, whereby the lens is protected as the probe is inserted into hard bony material.

6. An endoscopic pedicle probe as claimed in claim 3, wherein:

the lens is oriented to provide a view at 90° to the longitudinal axis of the probe.

7. An endoscopic pedicle probe as claimed in claim 3, wherein:

the lens is oriented to provide a forward view at 45° to the longitudinal axis of the probe.

8. An endoscopic pedicle probe as claimed in claim 3, wherein:

the lens is oriented to provide a straight-ahead forward view.

* * * * *